United States Patent [19]

Motoyama et al.

[11] 4,154,636

[45] May 15, 1979

[54] METHOD OF FILM-COATING MEDICINES

[75] Inventors: Shimesu Motoyama; Takuichi Tsujino, both of Tokyo, Japan

[73] Assignee: Freund Industrial Co., Ltd., Tokyo, Japan

[21] Appl. No.: 848,741

[22] Filed: Nov. 4, 1977

Related U.S. Application Data

[63] Continuation of Ser. No. 717,707, Aug. 25, 1976, abandoned.

[30] Foreign Application Priority Data

Aug. 27, 1975 [JP]   Japan ................... 50-103057

[51] Int. Cl.² ........................... A61K 9/28; B29C 6/02
[52] U.S. Cl. ..................................... 156/243; 53/441; 156/285; 424/35
[58] Field of Search ............... 156/243, 245, 285; 53/5, 26, 29, 30, 35, 36, 37; 424/14, 15, 16, 21, 31, 32, 33, 34, 35, 36, 37, 38, 39; 425/804; 427/3

[56] References Cited

U.S. PATENT DOCUMENTS

| | | | |
|---|---|---|---|
| 2,152,101 | 3/1939 | Scherer | 53/30 |
| 2,219,578 | 10/1940 | Pittenger | 53/30 |
| 2,275,654 | 3/1942 | Ravenscroft et al. | 53/30 |
| 2,387,747 | 10/1945 | Cowley | 53/30 |
| 2,497,212 | 2/1950 | Dunofrio | 53/30 |
| 2,503,518 | 4/1950 | Slaughter | 156/243 |
| 2,624,164 | 1/1953 | Dunofrio | 53/30 |
| 2,775,080 | 12/1956 | Stirn et al. | 53/30 |
| 3,523,907 | 8/1970 | Urancken et al. | 424/32 |
| 3,789,117 | 1/1974 | Tsujino | 424/35 |
| 3,909,444 | 9/1975 | Anderson et al. | 424/35 |

*Primary Examiner*—Caleb Weston
*Attorney, Agent, or Firm*—Blanchard, Flynn, Thiel, Boutell & Tanis

[57] ABSTRACT

A method of film-coating medicines which comprises either putting a prescribed dose of a medicine between two sheets capable of releasing the medicine wrapped therein within the digestive organs or putting a prescribed dose of a medicine in a tablet-shaped or capsule-shaped receptacle consisting of said film, and subsequently putting the films together so as to wrap the medicine therein.

8 Claims, 5 Drawing Figures

METHOD OF FILM-COATING MEDICINES

This is a continuation of application Ser. No. 717,707 filed Aug. 25, 1976.

BACKGROUND OF THE INVENTION

1. Field of the Invention

The present invention relates to a method of film-coating medicines, and particularly it relates to a method of film-coating which comprises putting a prescribed dose of a medicine between two sheets capable of releasing said medicine wrapped therein within the intestines or securing it in a receptacle formed of said film as the film-forming substance, and then putting the two films together by fusion or adhesion.

2. Description of the Prior Art

The film-coating method has hitherto been widely used because it has such advantages that, because a high-molecular film-forming substance is used, the resulting film is stable, and, because of the adoption of the hand-coating process or the spray process in applying an organic solvent solution of said substance, the operation is simple.

However, the conventional film-coating method has been defective in that, (1) inasmuch as it employs a process comprising dissolving said film-forming substance in an organic solvent or water and forming a coating film with the resulting solution, the object-to-be-coated must have a shape like a tablet and, accordingly, it has been impossible to apply a film-coating directly to a pulverized or a liquid medicine; (2) in the case of employing the spray process, since the bore of the nozzle for spraying is limited and the viscosity of the film-forming solution is restricted, in order to facilitate the spraying, it is required to lower the viscosity of the film-forming solution and it is inevitable to reduce the molecular weight thereof, causing deterioration of the strength of the resulting film and the occurrence of cracks therein, and moreover, inasmuch as the coating layer consists of spray particles, it is fragile and apt to exfoliate; (3) when an organic solvent is employed in the coating process, there is a fear of causing various troubles such as explosion or fire, public nuisance owing to the exhaust gas as well as the waste water, the question of employee health related to inhalation by working personnel, etc.; and (4) since the stamping or printing of minute letters or marks on every tablet is usually performed after finishing the coating, it has been difficult to ensure a definite, fine indication on the spherical surface of the resulting tablet.

SUMMARY OF THE INVENTION

The present invention is intended to eliminate the foregoing drawbacks of the film-coating method in the prior art.

The present invention provides a method of coating employing a film prepared beforehand as the film-forming substance, which will render it possible to perform the coating on even pulverized and liquid medicines, not to tablets. Moreover, it renders it possible to provide a stable coating layer superior in uniform resilience, impact resistance and abrasion resistance by selecting the film-forming material, and it also provide a desired thickness of said layer. Furthermore, not only the drawbacks of the prior art with respect to the safety of operation, the management of health of working personnel, the public nuisance, etc. can be eliminated because no organic solvent is employed at the time of coating, but also beautiful, distinct letters, marks or figures can be provided on the resulting tablet because it is possible to perform the printing on a prepared film by lithography prior to the coating. It is also possible to provide concave or convex letters, marks or figures on the surface of the film at the time of molding it in accordance with the shape of the desired tablet.

In other words, the present invention provides a method of coating medicines utilizing a film prepared beforehand as the film-forming substance, which method comprises preparing a double layer of film free of virulence and capable of releasing a medicine wrapped therein within the digestive organs, putting a prescribed dose of a medicine in between said double layer or putting a prescribed dose of a medicine in a receptacle prepared by molding the films into tablet-shape, capsule-shape or the like and then covering up the receptacle containing said medicine, and subsequently securing the films together by fusion or adhesion thereby effecting the coating.

DESCRIPTION OF THE PREFERRED EMBODIMENTS

Hereunder will be explained the details of the invention.

A film which is superior in transparency, glossiness, impact resistance, abrasion resistance, etc., free of virulence and capable of releasing a medicine wrapped therein within the intestines, is first prepared. As the substance to form a film having such properties, those substances which have hitherto been popular for use in film coating, e.g., cellulose acetate, phthalate, methyl cellulose, ethyl cellulose, hydroxypropyl cellulose, hydroxypropyl methyl cellulose, etc. are of course applicable, yet the use of thermoplastic macromolecular substances like everyone of the grades L, S, D of FUDRAGIT (registered trade mark of the products of ROHM PHARA Co., Germany), M.P.M. (registered trade mark of the manufacture of TANABE SEIYAKU K.K.), AEA (registered trade mark of the products of SANKYO SEIYAKU K.K.), etc. are preferable. It also will do to use one member or a mixture of plural members of the group consisting of polyvinyl acetate, polyvinyl alcohol, crotonic acid—methacrylic acid ester copolymer, polyethylene glycol, polyethylene, polyethylene—vinyl acetate copolymer, polypropylene, etc. A film formed of such a substance as above can be adjusted with respect to the speed of fusion or disintegration thereof according to the object of the medicine to be coated therewith, and also it can be easily adapted to a medicine intended for dissolving within the intestines or a medicine prescribed to have a prolonged efficacy. As an alternative, the use of a film which is not soluble or disintegrable in itself but has semi-permeability sufficient for releasing the medicine wrapped therein will do, and for this purpose, a filter material consisting of cellulose acetate, such as MILLIPORE FILTER (registered trade mark), is applicable.

A film for use as the film-forming substance is usually dissolved in a solvent and then molded into a film or a mold, but it also will do to melt it directly without using any solvent and mold the melt into a film or a mold. The film for use in the present invention is, as a rule, free from water or a solvent at the time of charging a medicine; yet, this rule does not of course apply to a medicine which is not affected by a film or a mold containing water. Moreover, a film for use in the present invention may contain a plasticizer, sweetenings, spices, a hiding agent, a coloring material added thereto as occasion demands, and also can be imparted with rubber-like elasticity and/or thermal contractility.

The present invention provide a method of effecting the coating which comprises stratifying two sheets of the film prepared as above or molding the prepared film into a box and a cover according to the shape of the tablet-to-be-coated, putting a prescribed dose of a medicine in between the stratified films or in the molded box with cover, and making the two sheets of film or the box and the cover adhere closely to each other. The present invention relates to a method of coating utilizing a film having specific properties as the film-forming substance, and its object is different from that of a method of wrapping a medicine by using a film as a wrapping material. That is, the coated tablet in the present invention can be swallowed as it is.

As the known methods resembling the method of the present invention, there are the soft capsule method and the hard capsule method. However, since these methods employ a gelatin sheet containing several score percent of water as the film-forming substance and are therefore unsuitable for a medicine that is vulnerable to hydrolysis, a medicine that is apt to be influenced by water and a water-soluble liquid medicine, they are different from the method of the present invention. According to the method of the present invention, the coating can be effected with respect to any liquid medicine, as well as hydrolyzable medicines.

As to the process of putting a prescribed dose of a medicine in between a double layer of film, there are various modes thereof such as, for instance, a mode wherein a prescribed dose of a medicine (plane tablet or powder) is placed at regular intervals on a sheet of film and another sheet of film is laid thereon; a mode wherein a prescribed number of recesses are formed at regular intervals on a sheet of film, a medicine (plane tablet, powder or liquid medicine) is accommodated in every recess and then another sheet of film is laid thereon; etc. Moreover, there are conceivable a mode wherein more than two sheets of film are stratified, and a mode wherein a medicine once coated is further coated with another film according to the intended use of the medicine. Besides, it is possible to subject a tablet once coated to stamping by means of a double-tablet molding machine, or form a different kind of film on the thus produced double-tablet.

As to the process of making the layered films adhere to each other or making the molded receptacle adhere to the cover thereof, there are conceivable various processes, such as the thermal adhesion process, the pressure adhesion process utilizing an adhesive or gas atmosphere having the effect of melting the film, etc. For instance, in the case of a polyacrylic acid type film, sealing can be effected by pressure adhesion in an atmosphere of methylene chloride gas. The inner surface of the mold to perform the sealing is preferably precoated with a fluorine resin or silicone resin in order to improve the mold releasability of the film.

Next, as an embodiment of the present invention, a method of coating which comprises feeding two sheets of film to a pair of rolls which are disposed to come in touch with each other and which rotate in opposite directions and putting said films together by virtue of the rotation of the rolls thereby to accommodate a plane tablet in between the thus interlocked films, will be hereunder explained with reference to the appended drawings.

Figure 1:
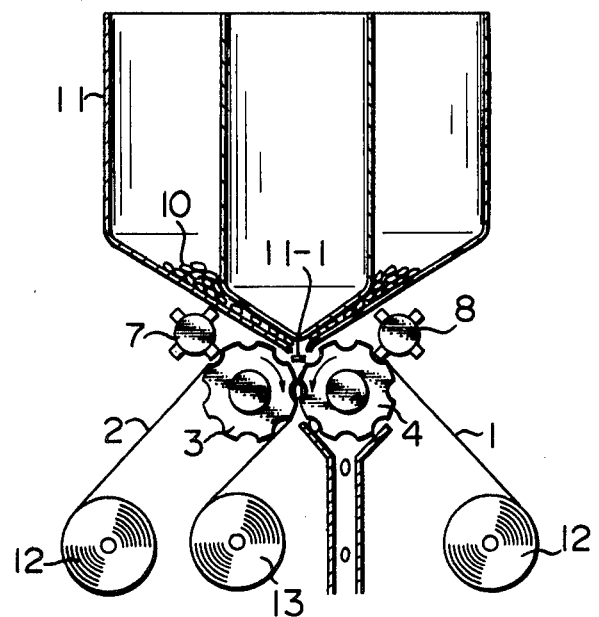
FIG. 1 illustrates the essential parts of a vertical apparatus useful in practicing the film-coating method of the present invention.
Figure 2:
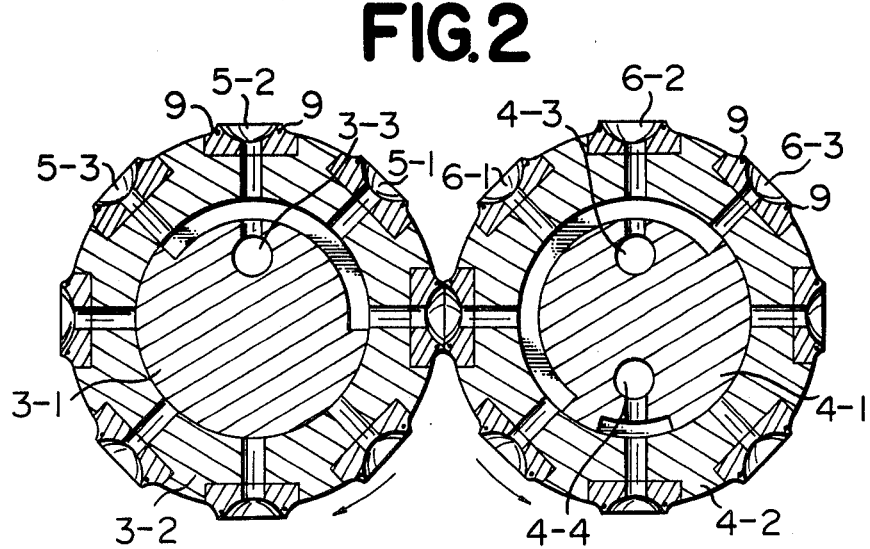
FIG. 2 is a schematic representation of an enlarged sectional view of the rolls 3, 4 in FIG. 1.
Figure 3:
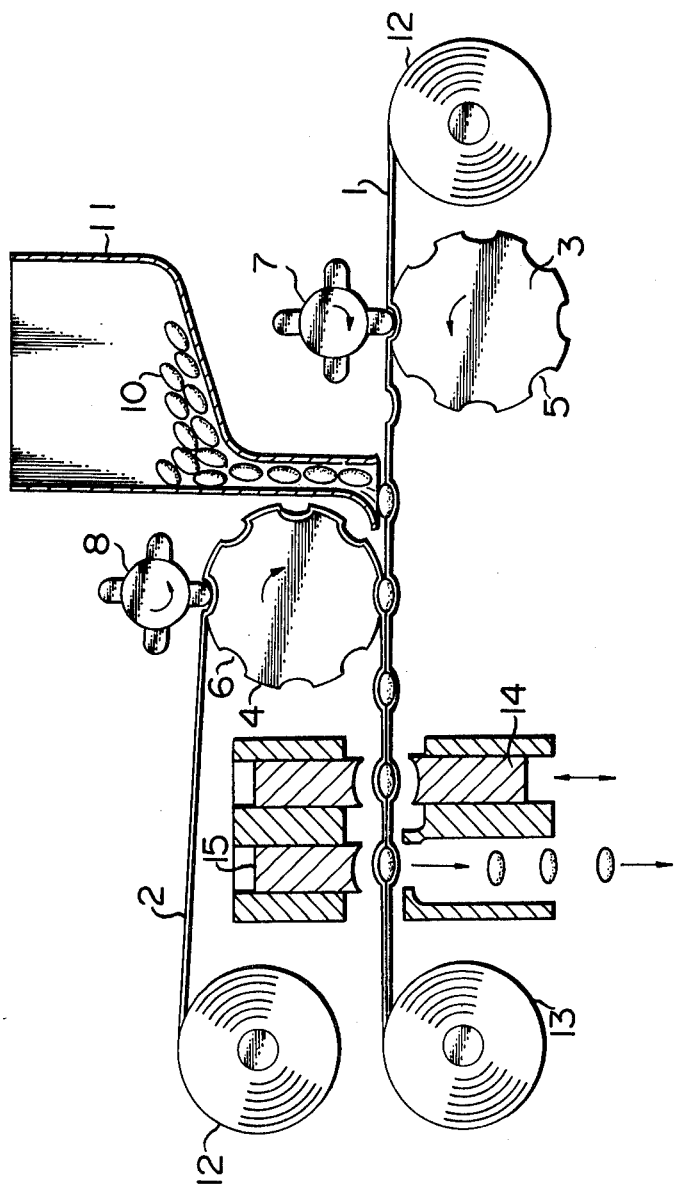
FIG. 3 is illustrates the essential parts of a horizontal apparatus useful in practicing the film-coating method of the present invention.

In this embodiment of the method of the present invention, two sheets of films 1, 2 are fed in between a pair of contacting rolls 3, 4 and film-coating is effected by virtue of the rotation of said rolls 3 there, 4. On the surface of the roll 3 are plurality of recesses 5, namely, 5-1, 5-2, ... 5-8, in the shape of one-half of the tablet-to-be-coated respectively, while on the surface of the other roll 4 contacting with the roll 3 and having the same diameter there are provided the same number of recesses 6, namely, 6-1, 6-2, ... 6-8, corresponding to the other one-half of the tablet-to-be-coated so as to form the shape of one tablet respectively when united with the recesses 5.

The rolls 3, 4 are constructed such that the center shafts 3-1, 4-1 are fixed while the outer portions 3-2, 4-2 of the rolls 3, 4 are rotatable. When these rotatable portions 3-2, 4-2 rotate and the recesses 5, 6 are located at the upper part of the shafts 3-1, 4-1, respectively, air is sucked in by the air suction portions 3—3, 4—3 provided on the shafts 3-1, 4-1, whereby the films 1, 2 are made to adhere closely to the surface of the rolls 3, 4 and, at the same time, the molding rolls 7, 8 engage with the rolls 3, 4, whereby the films 1, 2 are imparted with a recess modeled after the dents 5, 6, respectively. Moreover, the recesses 5, 6 of the rolls 3, 4 are respectively provided with an impulse heater 9 so that, when the surfaces of the rolls 3, 4 come in contact, electricity is turned on whereby the films 1, 2 adhering closely to the recesses 5, 6 are electrically fused. When the rolls 3, 4 further rotate and the recess 6 is located under the shaft 4-1, air is discharged through the air discharge portion 4—4 provided on the shaft 4-1 and said air is blown out into the recess 6, and the coated medicine is discharged from the recess 6 and falls.

Above the rolls 3, 4 is disposed a hopper 11 accommodating plane tablets of medicine 10-1, 10-2, ... 10-n.

The plane tablets 10 fall intermittently with intermittent opening and closing of the opening/closing plate provided at the bottom of the hopper 11, and are charged in between the recesses 5, 6 of the rolls 3, 4 with the films 1, 2 adhering closely thereto immediately before said recesses 5, 6 are united. The instant a plant tablet 10 goes in between the recesses 5, 6 and the recesses 5, 6 are united, the impulse heater 9 works, electricity is turned on to fuse the films, and the plane tablet 10 is coated with the films 1, 2 acting as the film-forming substance. The films 1, 2 excluding their portion used in the coating as the film-forming substance are wound round a winding roll 13.

A plane tablet 10 charged in between the confronting recesses 5, 6 enters the confronting recesses of the films 1, 2 stretched from the rewinding (or backfeed) roll 12 onto the surface of the rolls 3, 4—to wit, the recesses of the films 1, 2 formed within the dents 5, 6 of the rolls 3, 4 by means of the molding rolls 7, 8—and is united with the films 1, 2 fused by the impulse heater 9, whereby the film-coating is effected.

The speed of rotation of the films 1, 2 by means of the rolls 3, 4 and the opening/closing time of the opening/closing plate 11-1 for the purpose of charging the plane tablets 10 accommodated in the hopper 11 into the recesses 5, 6 are adjusted to ensure that the plane tablet 10 that is discharged from the hopper 11 should be exactly charged into the recesses 5, 6 and the film-coating be effected satisfactorily. In this way, the plane tablet 10 is subjected to film-coating, and through continuous operation of this process, a multiplicity of plane tablets can be film-coated continuously. Through modification of the hopper 11 in the illustrated apparatus, the film-coating of powders as well as liquid medicines becomes possible. Moreover, by varying the shape of the recesses 5, 6, there can be produced coated medicines of various shapes as desired.

The above explanation pertains to the case where a film is applied as it is as the film-forming substance. In addition to this mode of application of the film, it is also possible to mold the film into a tablet-shaped box and a cover thereof beforehand, charge a prescribed dose of a powder or a liquid medicine, as well as a plane tablet, into the thus prepared box and fix the cover thereby effecting the film-coating.

Figure 4:
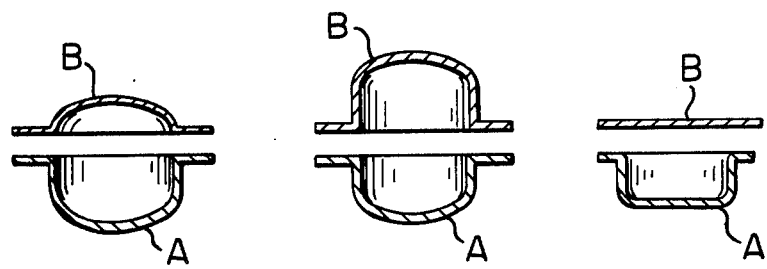
FIG. 4 and FIG. 5 illustrate examples of the receptacle to be used as the coating substance in the present invention.
Figure 5:
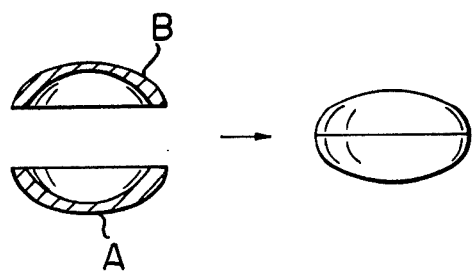

To be precise, a box A and a cover B prepared beforehand by molding the film as illustrated in FIGS. 4 and 5. Subsequently, the medicine is charged in between the B and the cover B, the cover B is put on the box A, and then the edges of the box A and cover B are made to adhere by a known method.

According to the present invention, it is rendered possible to perform the film-coating with respect to powder, liquid medicines and so forth, as well as tablets having a definite shape. It is also possible to provide a film coating having superior physical properties such as uniformity, elasticity, impact resistance, abrasion resistance, etc. required for the coating layer by selecting appropriate substances for use as the material for the film. Moreover, the present invention provides an excellent coating method which can be practiced without causing any trouble with respect to the management of health of working personnel, the question of public nuisance, etc.

EXAMPLE 1.

| | |
|---|---|
| polyvinyl alcohol (degree of saponification: 80%) | 15% (W/W) |
| glycerin | 3% |
| titanium oxide | 0.5% |
| water | balance |
| total | 100% |

By applying the above mixing ratio, polyvinyl alcohol and glycerin were first dissolved in water, and then titanium oxide was added to the resulting solution and dispersed uniformly therein by means of a homogenizer, whereby there was obtained a white, opaque and slightly viscous liquid. Subsequently, this liquid was spread thinly on a smooth polytetrafluoroethylene sheet and dried within a hot air drier at a temperature of 50-60° C. The resulting dry film was white in color, readily soluble in water, and 0.05 mm in thickness.

The thus prepared film was used as the film-forming substance in the coating method of the present invention. To begin with, printing was performed on this white film with a tablet printing ink (the manufacture of F.G. OKIE Inc., U.S.A.) by using an offset printing machine. As a result, even a minute letter of point 7 type could be printed very distinctly. Next, the thus printed film was wound round the rolls 3, 4 as illustrated in FIG. 1, and on this occasion, a modicum of dry starch was scattered so as to prevent the occurrence of interblocking of films.

Subsequently, by using this film, the coating was continuously performed on a multiplicity of tablets of 9 mm in diameter and 300 mg each in weight having corn-shaped curved surface. On this occasion, the pitch of the printing was adjusted to the pitch of the tablet placed on the rolls 3, 4 so as to locate the printed letters (or mark) at the center of every tablet, and rectification was performed with a phototube by utilizing a mark on the film in the same way as in the conventional SP packing machine. Adhesion of the film was effected by thermal adhesion at a temperature of 130°-140° C. utilizing the impulse heater provided within the rolls 3, 4.

EXAMPLE 2.

| | |
|---|---|
| methyl methacrylate-methacrylic acid copolymer | 20% (W/W) |
| triacetin | 2% |
| polyethylene glycol #6000 | 2% |
| titanium oxide | 1% |
| Lake color (food color No.4) | 0.5% |
| isopropyl alcohol ⎫ at the ratio of 1:1 | balance |
| acetone ⎭ | |
| total | 100% |

By applying the above mixing ratio and the same procedure as in Example 1, a yellow film was prepared. And, this film was used as the film-forming substance in providing a film-coating which can be digested within the intestines.

EXAMPLE 3.

| | |
|---|---|
| hydroxypropyl methyl cellulose-phthalic acid ester copolymer | 15% (W/W) |
| polyvinyl acetate resin | 7% |
| polyethylene glycol | 2% |
| titanium oxide | 1% |
| Lake color food color No.4) | 0.5% |
| orange essence | 0.5% |
| ethyl alcohol ⎫ at the ratio of 1:1 | balance |
| methylene chloride ⎭ | |
| total | 100% |

By applying the above mixing ratio and the same procedure as in Example 1, an orange-colored film having the smell of an orange was prepared. And, this film was used as the film-forming substance in providing a film-coating which can be digested within the intestines.

EXAMPLE 4.

| | |
|---|---|
| polyvinyl acetal-dimethylaminoacetate [AEA (registered trade mark); the manufacture of SANKYO SEIYAKU K.K.] | 18% (W/W) |
| polyethylene glycol #4000 | 5% |
| food color Blue No. 1 | 0.01% |
| acetone ⎫ at the ratio of 2:1 | balance |
| ethyl alcohol ⎭ | |

| | |
|---|---|
| total | 100% |

By applying the above mixing ratio, a transparent, blue-colored film insoluble in water but easily soluble in acid was obtained. This film was used in coating as the film-forming substance.

All of the films prepared in the foregoing Examples 1 through 4 have proved effective for providing a desired film-coating, and the results have been satisfactory without exception.

What is claimed is:

1. A method of film-coating a medicine, which comprises providing a pair of preformed thermoplastic resin films which are substantially free of water and solvent, said films being made of a material which is safe for human consumption and is capable of releasing medicine contained therein when contacted by gastro-intestinal fluid, said films being heat sealable to each other; feeding said films onto the peripheries of a pair of counter-rotating, radially opposed, capsule-forming rolls at least one of which has recesses in its periphery which recesses successively mate with peripheral portions of the other capsule-forming roll at the nip of said capsule-forming rolls to form capsule-forming cavities; as said films move with said capsule-forming rolls, moving the film associated with a cavity-forming roll having said recesses therein past a molding roll having molding elements projecting radially from the periphery thereof so that said elements successively contact portions of said film and force same into the recesses of the associated capsule-forming roll whereby to form pockets in said film; continuing to move said films with said capsule-forming rolls in converging paths toward the nip of said capsule-forming rolls and depositing a charge of medicine between said films; then moving said films into the nip of said capsule-forming rolls whereat the peripheries of said capsule-forming rolls contact each other to define a closed capsule-forming cavity and simultaneously electrically heating said contacting portions around the margin of said cavity by electrically energizing electric heaters located in said rolls close to said contacting portions to fuse said films together thereat whereby to form a closed capsule containing said charge of medicine; and then removing said capsule from the remainder of said films.

2. A method according to claim 1 in which said films consist essentially of a water-soluble resin.

3. A method according to claim 1 in which said sheets films consist essentially of cellulose acetate and have fine pores therethrough so as to be pervious to the medicine.

4. A method according to claim 1 in which said films consist essentially of a material selected from the group consisting of cellulose acetate, phthalic acid esters, methyl cellulose, ethyl cellulose, hydroxy propyl cellulose, hydroxy propyl methyl cellulose, polyvinyl acetate, polyvinyl alcohol, crotonic acid-methacrylic acid ester copolymer, methyl methacrylate-methacrylic acid copolymer, polyethylene glycol, polyethylene, polyethylenevinyl acetate copolymer, polypropylene and mixtures thereof.

5. A method according to claim 1 in which said films consist essentially of polyvinyl alcohol.

6. A method according to claim 1 in which said films consist essentially of a mixture of methyl methacrylate-methacrylic acid copolymer and polyethylene glycol.

7. A method according to claim 1 in which said films consist essentially of a mixture of hydroxypropyl methyl cellulose-phthalic acid ester copolymer, polyvinyl acetate and polyethylene glycol.

8. A method according to claim 1 in which said films consist essentially of a mixture of polyvinyl acetal-dimethylaminoacetate and polyethylene glycol.

* * * * *

UNITED STATES PATENT AND TRADEMARK OFFICE
CERTIFICATE OF CORRECTION

PATENT NO. : 4 154 636
DATED : May 15, 1979
INVENTOR(S) : Shimesu Motoyama et al It is certified that error appears in the above-identified patent and that said Letters Patent are hereby corrected as shown below:

Column 8, line 12; delete "sheets".

Signed and Sealed this

Fourteenth Day of August 1979

[SEAL]

Attest:

Attesting Officer

LUTRELLE F. PARKER
Acting Commissioner of Patents and Trademarks